(12) United States Patent
Kubo

(10) Patent No.: US 10,940,293 B2
(45) Date of Patent: Mar. 9, 2021

(54) CATHETER AND BALLOON CATHETER

(71) Applicant: ASAHI INTECC CO., LTD., Seto (JP)

(72) Inventor: Yuta Kubo, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 408 days.

(21) Appl. No.: 15/682,894

(22) Filed: Aug. 22, 2017

(65) Prior Publication Data

US 2018/0140808 A1 May 24, 2018

Related U.S. Application Data

(63) Continuation of application No. PCT/JP2016/084835, filed on Nov. 24, 2016.

(51) Int. Cl.
*A61M 25/10* (2013.01)
*A61M 25/01* (2006.01)
*A61M 25/00* (2006.01)
*A61F 2/958* (2013.01)

(52) U.S. Cl.
CPC ......... *A61M 25/1029* (2013.01); *A61F 2/958* (2013.01); *A61M 25/005* (2013.01); *A61M 25/0045* (2013.01); *A61M 25/0053* (2013.01); *A61M 25/104* (2013.01); *A61M 25/1034* (2013.01); *A61M 25/0069* (2013.01);
(Continued)

(58) Field of Classification Search
CPC ............ A61M 25/1029; A61M 25/104; A61M 25/005; A61M 25/0051; A61M 25/0052; A61M 25/0053; A61M 25/0054; A61M 25/0059; A61M 25/0045; A61M 25/1034; A61M 25/0012; A61M 2025/1056; A61M 2025/1068; A61M 2025/1084; A61M 2025/09083; A61M 25/008; A61M 25/10
USPC ................................................. 604/524–527
See application file for complete search history.

(56) References Cited

U.S. PATENT DOCUMENTS 5,728,063 A * 3/1998 Preissman ........... A61M 25/005
604/103.09
5,879,342 A * 3/1999 Kelley ................ A61M 25/005
600/524
(Continued)

FOREIGN PATENT DOCUMENTS

CN 104857617 A 8/2015
CN 106422024 A 2/2017
(Continued)

*Primary Examiner* — Katherine H Schwiker
(74) *Attorney, Agent, or Firm* — Oblon, McClelland, Maier & Neustadt, L.L.P.

(57) ABSTRACT

A catheter that includes a reinforcing body including a wire wound or woven so that a gap is provided between each winding or weave of the wire; an inner layer, the reinforcing body being embedded in at least a part of the inner layer; and an outer layer that covers an outer periphery of the inner layer in a circumferential direction, and the reinforcing body is formed integrally including a first diameter portion with a first outer diameter, a second diameter portion with a second outer diameter larger than the first outer diameter, and a tapered portion increasing in diameter toward a distal end side or a proximal end side between the first diameter portion and the second diameter portion, and at least the second diameter portion of the reinforcing body is embedded in the outer layer.

18 Claims, 13 Drawing Sheets

(52) U.S. Cl.
CPC ............... *A61M 2025/0183* (2013.01); *A61M 2025/1056* (2013.01); *A61M 2025/1068* (2013.01)

(56) References Cited

U.S. PATENT DOCUMENTS

| | | | |
|---|---|---|---|
| 6,090,099 A * | 7/2000 | Samson | A61M 25/0045 604/527 |
| 6,186,978 B1 * | 2/2001 | Samson | A61M 25/005 604/525 |
| 6,193,705 B1 * | 2/2001 | Mortier | A61M 25/0041 604/264 |
| 7,331,948 B2 | 2/2008 | Skarda | |
| 2002/0156459 A1 * | 10/2002 | Ye | A61L 29/085 604/527 |
| 2002/0198491 A1 * | 12/2002 | Miller | A61M 25/005 604/96.01 |
| 2005/0283136 A1 | 12/2005 | Skarda | |
| 2011/0245775 A1 * | 10/2011 | Tekulve | A61M 25/0045 604/171 |
| 2012/0271232 A1 * | 10/2012 | Katsurada | A61M 25/0052 604/103.09 |
| 2014/0107575 A1 * | 4/2014 | Miller | A61M 25/005 604/103.09 |
| 2014/0214006 A1 * | 7/2014 | Hiroshige | A61M 25/0012 604/527 |
| 2015/0231360 A1 * | 8/2015 | Watanabe | A61M 25/0053 604/527 |
| 2015/0231375 A1 * | 8/2015 | Kubo | A61M 25/008 604/96.01 |
| 2016/0235941 A1 * | 8/2016 | Matsumoto | A61M 25/0012 |
| 2017/0043119 A1 * | 2/2017 | Kubo | A61M 25/10 |
| 2017/0072163 A1 * | 3/2017 | Lim | A61M 25/005 |

FOREIGN PATENT DOCUMENTS

| | | |
|---|---|---|
| JP | 2006-263289 A | 10/2006 |
| JP | 2012-249811 A | 12/2012 |
| JP | 2014-188338 A | 10/2014 |
| JP | 2014188338 A * | 10/2014 |
| JP | 2015-192808 A | 11/2015 |

* cited by examiner

CATHETER AND BALLOON CATHETER

CROSS REFERENCES TO RELATED APPLICATIONS

This is a continuation of International Application No. PCT/JP2016/084835, filed Nov. 24, 2016, the entire contents of which is incorporated herein by reference.

FIELD

The present disclosure relates to a catheter and a balloon catheter that are used to diagnose or treat a constricted portion or a blocked portion formed in a blood vessel or a digestive organ.

BACKGROUND

When a constricted portion or a blocked portion is formed in a blood vessel, a bile duct, a pancreatic duct, or the like, the flow of blood, bile (gall), pancreatic juice, and the like is deteriorated. As a method of diagnosing or treating such a constricted portion or blocked portion, a diagnosing method or a treating method using a catheter is performed widely.

The following Patent Literature 1 discloses a catheter in which an inner layer 11 covers an outer periphery of a reinforcing material 7, and an outer layer 12 covers an outer periphery of the inner layer 11 (see FIG. 3, etc.).

Moreover, the following Patent Literature 2 discloses a balloon catheter in which an outer layer 24b covers an outer periphery of a reinforcing material 24c, and an end of the reinforcing material 24c projects inside the outer tube 24b (see FIG. 4A, etc.).

However, the catheter described in Patent Literature 1 and the balloon catheter described in Patent Literature 2 have a problem that when pushed and pulled while the outer layer is caught by a constricted portion or a blocked portion, pressure is imposed on a joint portion between the outer layer and the inner layer, and the outer layer is easily separated from the inner layer.

CITATION LIST

Patent Document

Patent Document 1: Japanese Patent Application Laid-open No. 2006-263289
Patent Document 2: Japanese Patent Application Laid-open No. 2015-192808

SUMMARY

According to one aspect of the disclosure, there is provided a catheter, comprising: a reinforcing body including a wire wound or woven so that a gap is provided between each winding or weave of the wire; an inner layer extending in a longitudinal direction, the reinforcing body being embedded in at least a part of the inner layer; and an outer layer that covers an outer periphery of the inner layer in a circumferential direction, wherein the reinforcing body is formed integrally including a first diameter portion with a first outer diameter, a second diameter portion with a second outer diameter larger than the first outer diameter, and a tapered portion increasing in diameter toward a distal end side or a proximal end side between the first diameter portion and the second diameter portion, and at least the second diameter portion of the reinforcing body is embedded in the outer layer.

DESCRIPTION OF EMBODIMENTS

Technical Problem

Figure 1:
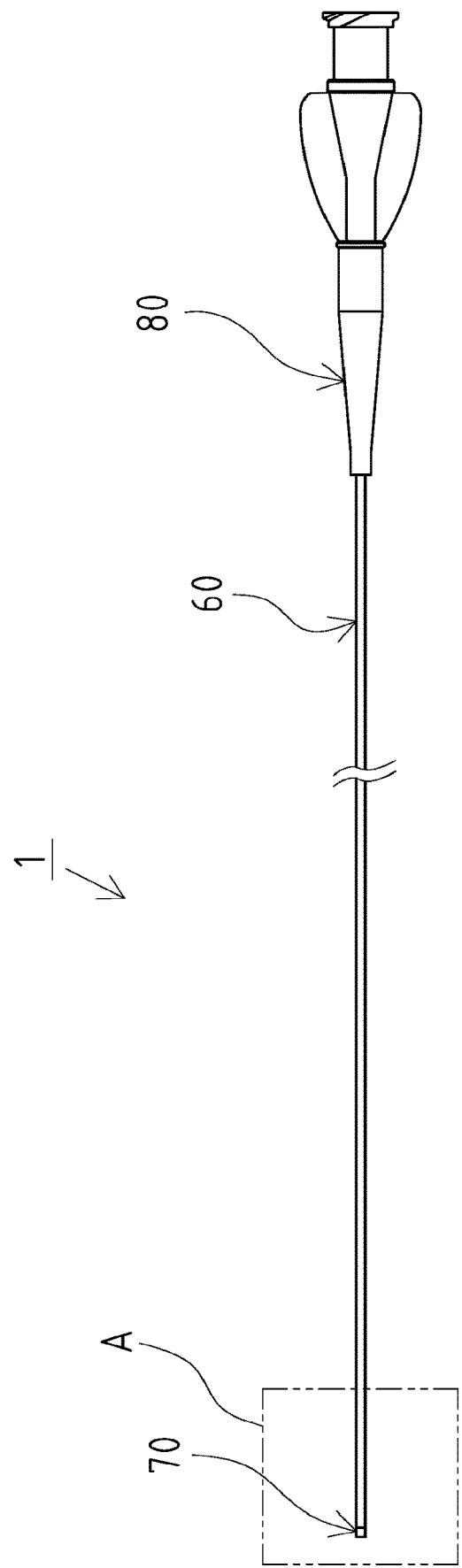
FIG. 1 is an entire view illustrating the entire of a catheter according to a first embodiment.

In view of such an aspect, the present disclosure aims at providing a catheter and a balloon catheter capable of preventing the outer layer from separating from the inner layer even in the case where the outer layer is pulled in an axis direction (distal end direction and proximal end direction).

Solution to Problem

The above-described problems are solved by the following means.

The first aspect of the disclosure is a catheter, including a reinforcing body that is formed by winding or weaving a wire so that a gap is provided between the adjacent wire, an inner layer that covers an outer periphery of the reinforcing body, and an outer layer that covers an outer periphery of the inner layer, in which the reinforcing body is formed integrally including a small diameter portion with a first outer diameter, a large diameter portion with a second outer diameter larger than the first outer diameter, and a tapered portion increasing in diameter toward a distal end side or a proximal end side between the small diameter portion and the large diameter portion, and at least the large diameter portion of the reinforcing body is embedded in the outer layer.

The second aspect of the disclosure is a balloon catheter, including the catheter according to the first aspect, and a balloon that is joined to the outer layer on a side of the large diameter portion of the reinforcing body of the catheter, in which at a joint portion between the outer layer and the balloon, the balloon includes a concave and convex inner peripheral surface, and the convex portion of the balloon is embedded to the inner side than the second outer diameter of the reinforcing body in the gap.

The third aspect of the disclosure is a balloon catheter, including a reinforcing body that is formed by winding or weaving a wire so that a gap is provided between the adjacent wire, a resin layer that covers an outer periphery of the reinforcing body, and a balloon that is joined to an outer periphery of the resin layer, in which the reinforcing body is formed integrally including a small diameter portion with a first outer diameter, a large diameter portion with a second outer diameter larger than the first outer diameter on a distal end side than the small diameter portion, and a tapered portion increasing in diameter toward the distal end side between the small diameter portion and the large diameter portion, and at a joint portion between the resin layer and the balloon, the balloon includes a concave and convex inner peripheral surface, and at least the large diameter portion of the reinforcing body is embedded in the convex portion of the balloon.

Effect of the Disclosure

In the catheter according to the first aspect of the disclosure, the reinforcing body is formed integrally including a small diameter portion with a first outer diameter, a large diameter portion with a second outer diameter larger than the first outer diameter, and a tapered portion increasing in diameter toward a distal end side or a proximal end side between the small diameter portion and the large diameter portion, and at least the large diameter portion of the reinforcing body is embedded in the outer layer. Therefore, the anchoring effect between the large diameter portion of the reinforcing body increasing in diameter from the inner layer toward the outer layer and embedded in the outer layer and the outer layer can reduce a risk that the outer layer is separated from the inner layer even in the case where the outer layer is pulled in the axis direction (distal end direction and proximal end direction) by a constricted portion or a blocked portion.

In the balloon catheter according to the second aspect of the disclosure, at a joint portion between the outer layer and the balloon, the balloon includes a concave and convex inner peripheral surface, and the convex portion of the balloon is embedded to an inner side than the second outer diameter of the reinforcing body in the gap. Therefore, even in the case where the balloon is expanded and pulled outward, the anchoring effect by a catch of the wire reduces a risk that the balloon is separated from the outer layer.

In the balloon catheter according to the third aspect of the disclosure, the reinforcing body is formed integrally including a small diameter portion with a first outer diameter, a large diameter portion with a second outer diameter larger than the first outer diameter on a distal end side than the small diameter portion, and a tapered portion increasing in diameter toward the distal end side between the small diameter portion and the large diameter portion, and at a joint portion between the resin layer and the balloon, the balloon includes a concave and convex inner peripheral surface, and at least the large diameter portion of the reinforcing body is embedded in the convex portion of the balloon. Therefore, even in the case where the balloon is expanded and pulled outward, the anchoring effect by a catch of the wire reduces a risk that the balloon is separated from the resin layer.

Figure 2:
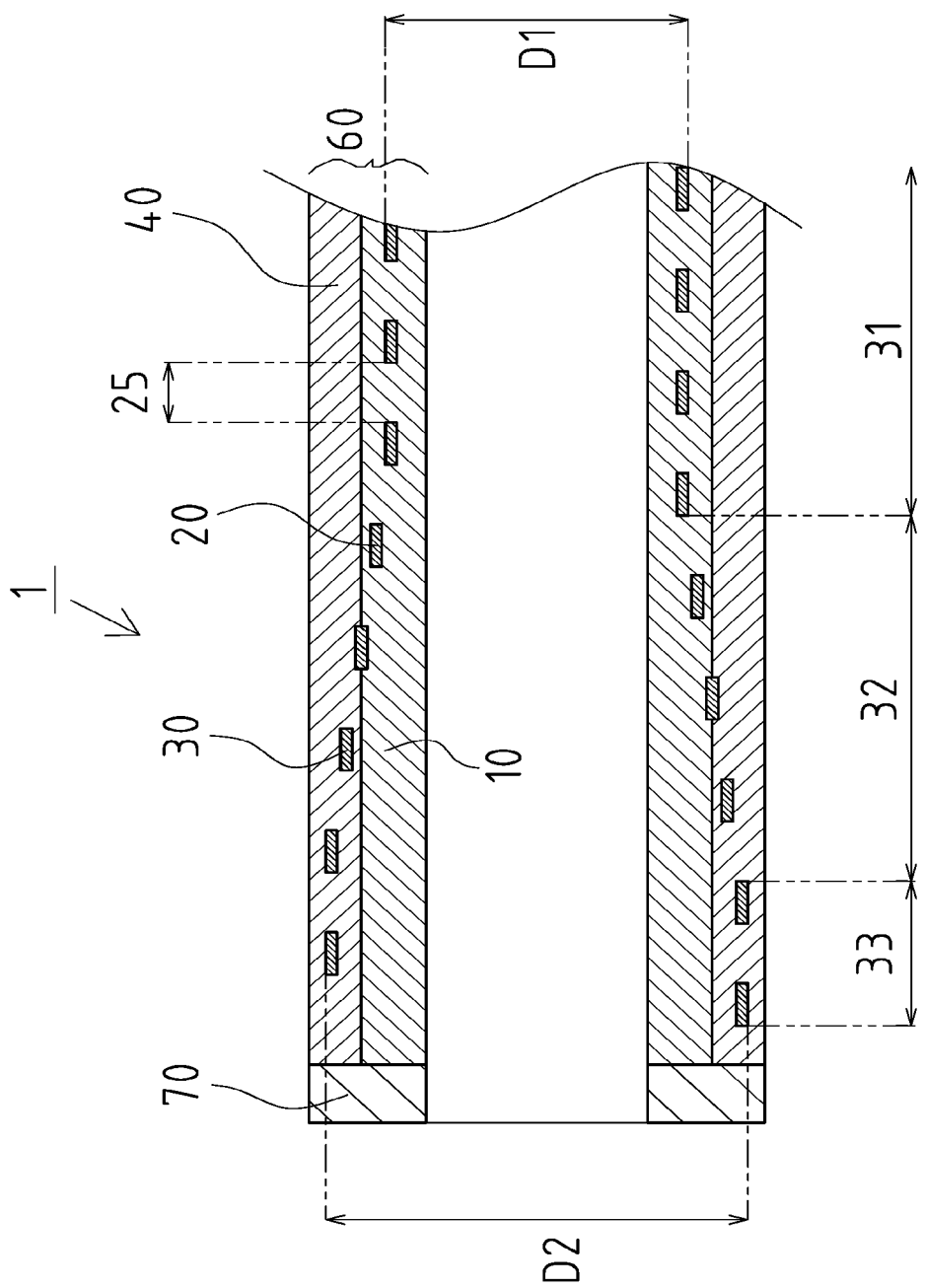
FIG. 2 is an enlarged section view of an A part of FIG. 1.
Figure 3:
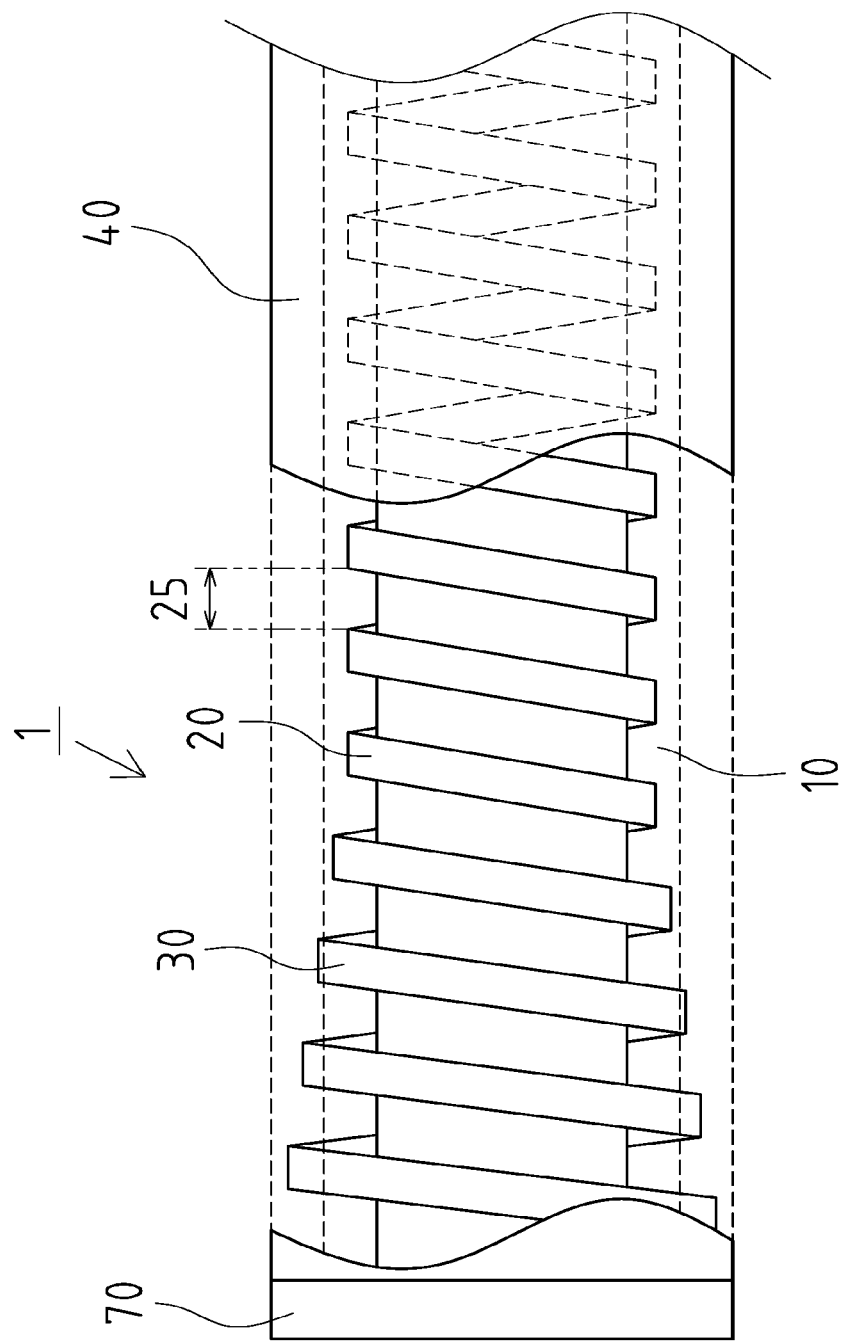
FIG. 3 is a schematic enlarged view of the A part of FIG. 1.

A catheter 1 according to a first embodiment will be described with reference to FIG. 1 to FIG. 3. In FIG. 1, the left side of the drawings is a distal end side (far side) to be inserted in a body, while the right side in the drawing is a proximal end side (near side) to be operated by a technician such as a physician. FIG. 2 is an enlarged view of an A part of FIG. 1. FIG. 3 is a schematic enlarged view of the A part of FIG. 1.

The catheter 1 is a catheter used to diagnose or treat a constricted portion or a blocked portion, for example. As illustrated in FIG. 1, the catheter 1 mainly includes a catheter shaft 60, a tip 70 joined to a distal end of the catheter shaft 60, and a connector 80 joined to a proximal end of the catheter shaft 60.

The catheter shaft 60 includes, in the order from the inner side in a radial direction, a reinforcing body (coil body) 30 wound by a wire 20 so as to have a gap 25 between the adjacent wire 20, an inner layer covering an outer periphery of the reinforcing body (coil body) 30, and an outer layer 40 covering an outer periphery of the inner layer 10a, as illustrated in FIG. 2 and FIG. 3. Note that to facilitate understanding, FIG. 3 illustrates a state in which the outer layer 40 and the inner layer 10 are peeled partially.

The inner layer 10 is formed of resin, and a guide wire or another catheter can be inserted therein. The resin material forming the inner layer 10 is not particularly limited, and polyamide, polyamide elastomer, polyester, polyurethane, polyethylene, or the like can be used.

The coil body 30 as a reinforcing body is provided in the inner layer 10. The coil body 30 is formed by winding a wire 20. As the material of the wire 20 forming the coil body 30, stainless steel (SUS304) is used in the first embodiment. However, the embodiment is not limited thereto. For example, there may be used not only a metal material such as tungsten or an Ni—Ti alloy but also a resin material such as reinforced plastic (PEEK). Note that the winding direction of the wire 20 forming the coil body 30 may be a clockwise direction or a counterclockwise direction toward the distal end side.

The outer layer 40 formed of resin is formed on the outer periphery of the inner layer 10, and covers the inner layer 10 and the reinforcing body (coil body) 30. The resin material forming the outer layer 40 is not particularly limited, and polyamide, polyamide elastomer, polyester, polyurethane, polyethylene, or the like can be used.

The tip 70 formed of resin is joined to the distal end of the above-described catheter shaft 60. The resin forming the tip 70 is not particularly limited, and polyurethane, polyurethane elastomer, or the like is used. Moreover, the tip 70 may contain radiopaque powder. For example, when the tip 70 contains radiopaque powder (e.g., tungsten powder) in a range of about 65 wt % to about 90 wt %, the technician such as a physician can accurately grasp a position of the catheter 1 in X-ray irradiation.

As illustrated in FIG. 2, the reinforcing body (coil body) 30 is formed integrally including a small diameter portion 31 having a first outer diameter D1, a large diameter portion 33 having a second outer diameter D2 larger than the first outer diameter D1, which is provided on the distal end side than the small diameter portion 31, and a tapered portion 32 increasing in diameter toward the distal end side between the small diameter portion 31 and the large diameter portion 33. The reinforcing body (coil body) 30 is raised from the inside of the inner layer 10 and embedded in the outer layer 40 at the large diameter portion 33 or at the tapered portion 32 and the large diameter portion 33.

In the catheter 1, the reinforcing body (coil body) 30 increases in diameter from the small diameter portion 31 toward the large diameter portion 33. The anchoring effect between the outer layer 40 and the wire 20 embedded therein, at the large diameter portion 33 or at the tapered portion 32 and the large diameter portion 33, can reduce a risk that the outer layer 40 is separated from the inner layer 10 even in the case where the outer layer 40 is pulled in the axis direction (distal end direction and proximal end direction) by an constricted portion or a blocked portion when the catheter 1 is inserted in a blood vessel, a bile duct, a pancreatic duct, or the like.

Note that in the first embodiment, the reinforcing body (coil body) 30 is made by winding the wire 20 around a core metal to form the small diameter portion 31 and then removing the core metal and expanding the wire on the distal end side from the inside to form the tapered portion 32 and the large diameter portion 33. However, the embodiment is not limited thereto. The wire 20 may be wound around a core metal to form the large diameter portion 33, and then a smaller core metal may be further inserted to form the tapered portion 32 and the small diameter portion 31 using a heat shrinkable tube.

Figure 4:
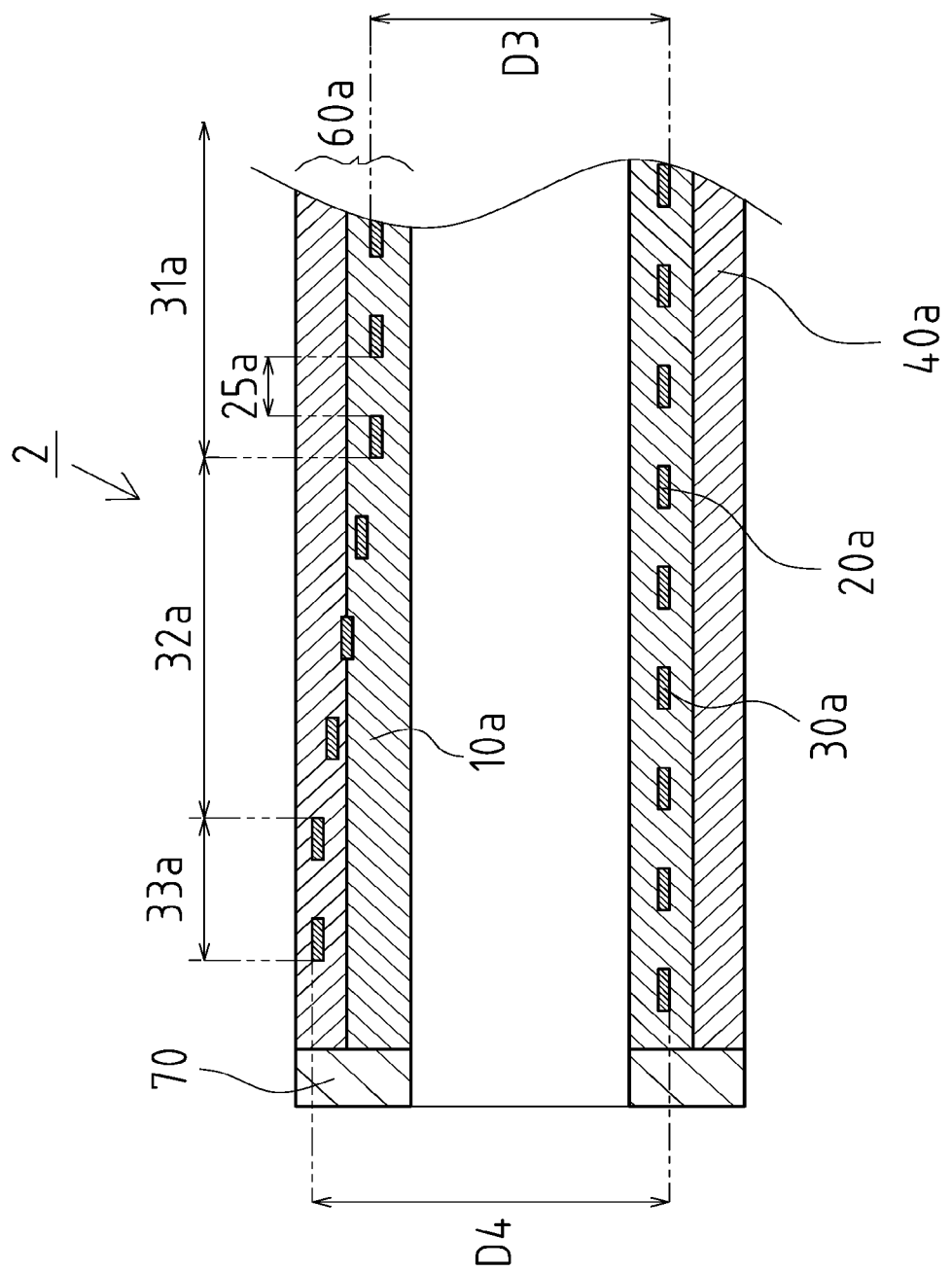
FIG. 4 is a section view corresponding to FIG. 2 of a catheter according to a second embodiment.

Next, a catheter 2 of the second embodiment will be described with reference to FIG. 4. Explaining only a difference from the catheter 1 illustrated in FIG. 2, in the catheter 2, a catheter shaft 60a includes, in the order from the inner side in a radial direction, a reinforcing body (coil body) 30a wound by a wire 20a so as to have a gap 25a between the adjacent wire 20a, an inner layer 10a covering an outer periphery of the reinforcing body (coil body) 30a, and an outer layer 40a covering an outer periphery of the inner layer 10a. The reinforcing body (coil body) 30a is formed integrally including a small diameter portion 31a having a first outer diameter D3, a large diameter portion 33a having a second outer diameter D4 larger than the first outer diameter D3, which is provided on the distal end side than the small diameter portion 31a, and a tapered portion 32a increasing in diameter toward the distal end side between the small diameter portion 31a and the large diameter portion 33a. In a part in a circumferential direction of the catheter shaft 60a, the reinforcing body (coil body) 30a is raised from the inside of the inner layer 10a and embedded in the outer layer 40a at the large diameter portion 33a or at the tapered portion 32a and the large diameter portion 33a.

In the catheter 2, the reinforcing body (coil body) 30a increases in diameter from the small diameter portion 31a toward the large diameter portion 33a in a part in a circumferential direction of the catheter shaft 60a, similarly to the catheter 1. The anchoring effect between the outer layer 40a and the wire 20a embedded therein, at the large diameter portion 33a or at the tapered portion 32a and the large diameter portion 33a, can reduce a risk that the outer layer 40a is separated from the inner layer 10a even in the case where the outer layer 40a is pulled in the axis direction (distal end direction and proximal end direction) by a constricted portion or a blocked portion when the catheter 2 is inserted in a blood vessel, a bile duct, a pancreatic duct, or the like.

Next, a catheter 3 of the third embodiment will be described with reference to FIG. 5 and FIG. 6. Explaining only a difference from the catheter 1 illustrated in FIG. 2 and FIG. 3, the catheter 3 includes, in the order from the inner side in a radial direction of a catheter shaft 60b, a reinforcing body (braid) 30b formed by mutually weaving a plurality of wires (a first wire 20b and a second wire 21b) so as to have a gap 25b between the adjacent first wire 20b or between the adjacent second wire 21b, an inner layer 10b covering an outer periphery of the reinforcing body (braid) 30b, and an outer layer 40b covering an outer periphery of the inner layer 10b. Note that to facilitate understanding, FIG. 6 illustrates a state in which the outer layer 40 and the inner layer 10 are peeled partially.

The reinforcing body (braid) 30b is formed by mutually weaving the first wire 20b and the second wire 21b in a net form (mesh form), and the first wire 20b and the second wire 21b are wound in a different direction from each other toward the distal end side. In the third embodiment, the total of 16 pieces (8 pieces×8 pieces) of wires including eight pieces of first wires 20b and eight pieces of second wires 21b are woven alternately to form the reinforcing body (braid) 30b. Here, the first wire 20b is a flat wire, while the second wire 21b is a round wire. However, the embodiment is not limited thereto, and both the first wire 20b and the second wire 21b may be round wires or flat wires.

The material of the first wire 20b and the second wire 21b forming the reinforcing body (braid) 30b may be same or different. In the third embodiment, there are used the first wire 20b formed of tungsten and the second wire 21b formed of stainless steel (SUS304). However, the embodiment is not limited thereto, and a resin material other than metal (e.g., reinforced plastic) may be used.

Figure 5:
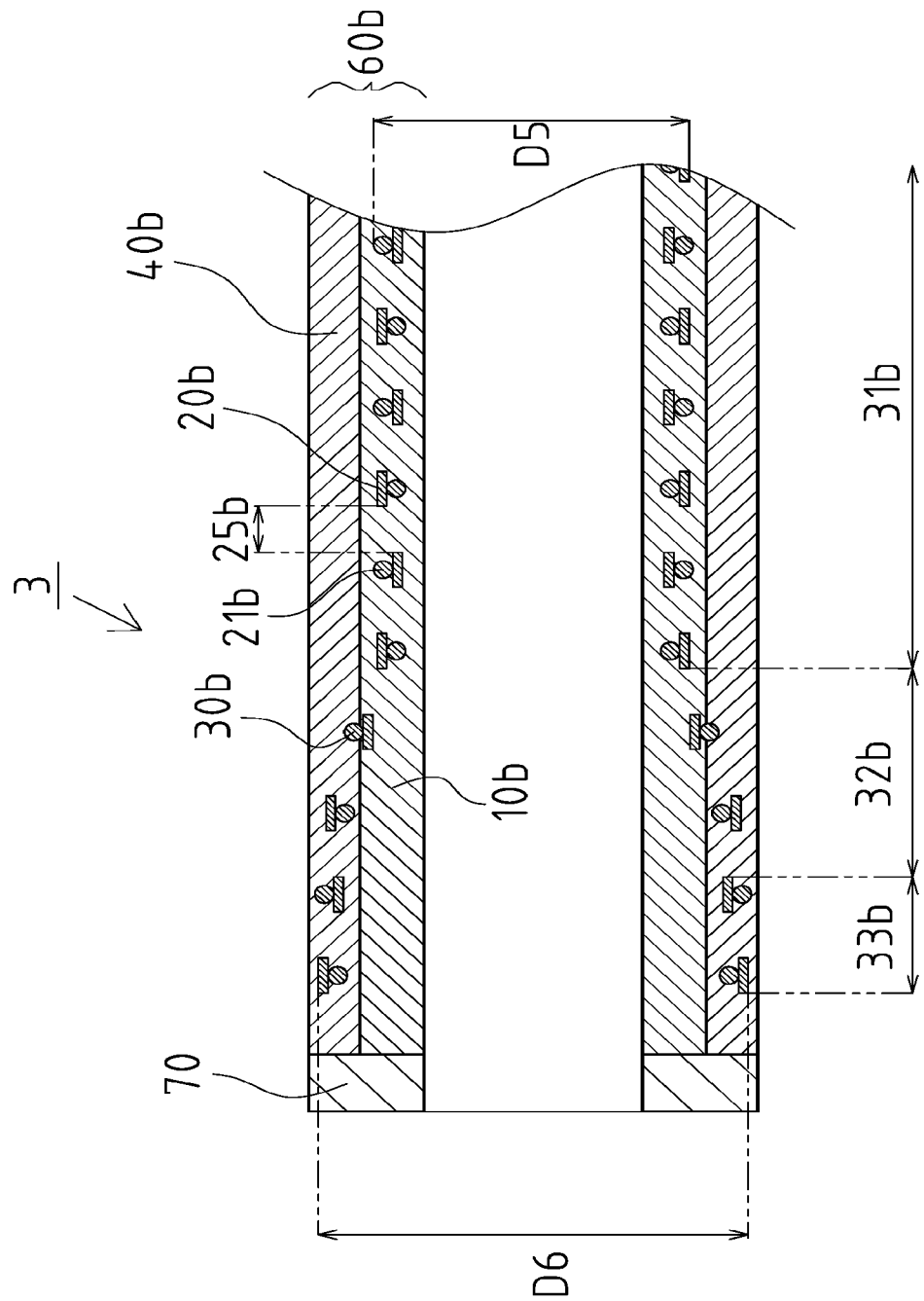
FIG. 5 is a section view corresponding to FIG. 2 of a catheter according to a third embodiment.
Figure 6:
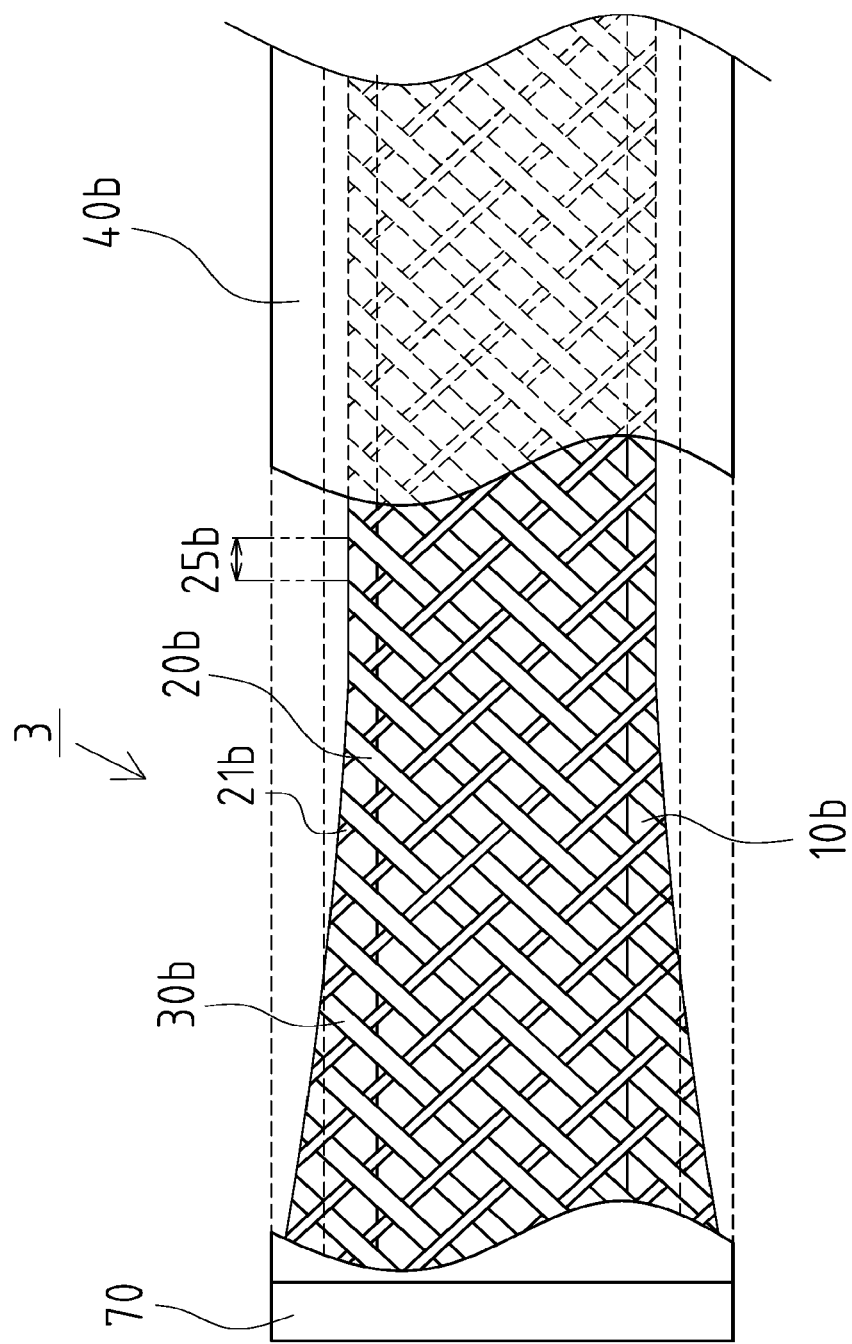
FIG. 6 is a section view corresponding to FIG. 3 of the catheter according to the third embodiment.

As illustrated in FIG. 5, the reinforcing body (braid) 30b is formed integrally including a small diameter portion 31b having a first outer diameter D5, a large diameter portion 33b having a second outer diameter D6 larger than the first outer diameter D5, which is provided on the distal end side than the small diameter portion 31b, and a tapered portion 32b increasing in diameter toward the distal end side between the small diameter portion 31b and the large diameter portion 33b. The reinforcing body (braid) 30b is raised from the inside of the inner layer 10b and embedded in the outer layer 40b at the large diameter portion 33b or at the tapered portion 32b and the large diameter portion 33b.

In the catheter 3, the reinforcing body (braid) 30b increases in diameter from the small diameter portion 31b toward the large diameter portion 33b. The anchoring effect between the outer layer 40b and the first wire 20b and the second wire 21b embedded therein, at the large diameter portion 33b or at the tapered portion 32b and the large diameter portion 33b, can reduce a risk that the outer layer 40b is separated from the inner layer 10b even in the case where the outer layer 40b is pulled in the axis direction (distal end direction and proximal end direction) by a constricted portion or a blocked portion when the catheter 3 is inserted to a blood vessel, a bile duct, a pancreatic duct, or the like.

Figure 7:
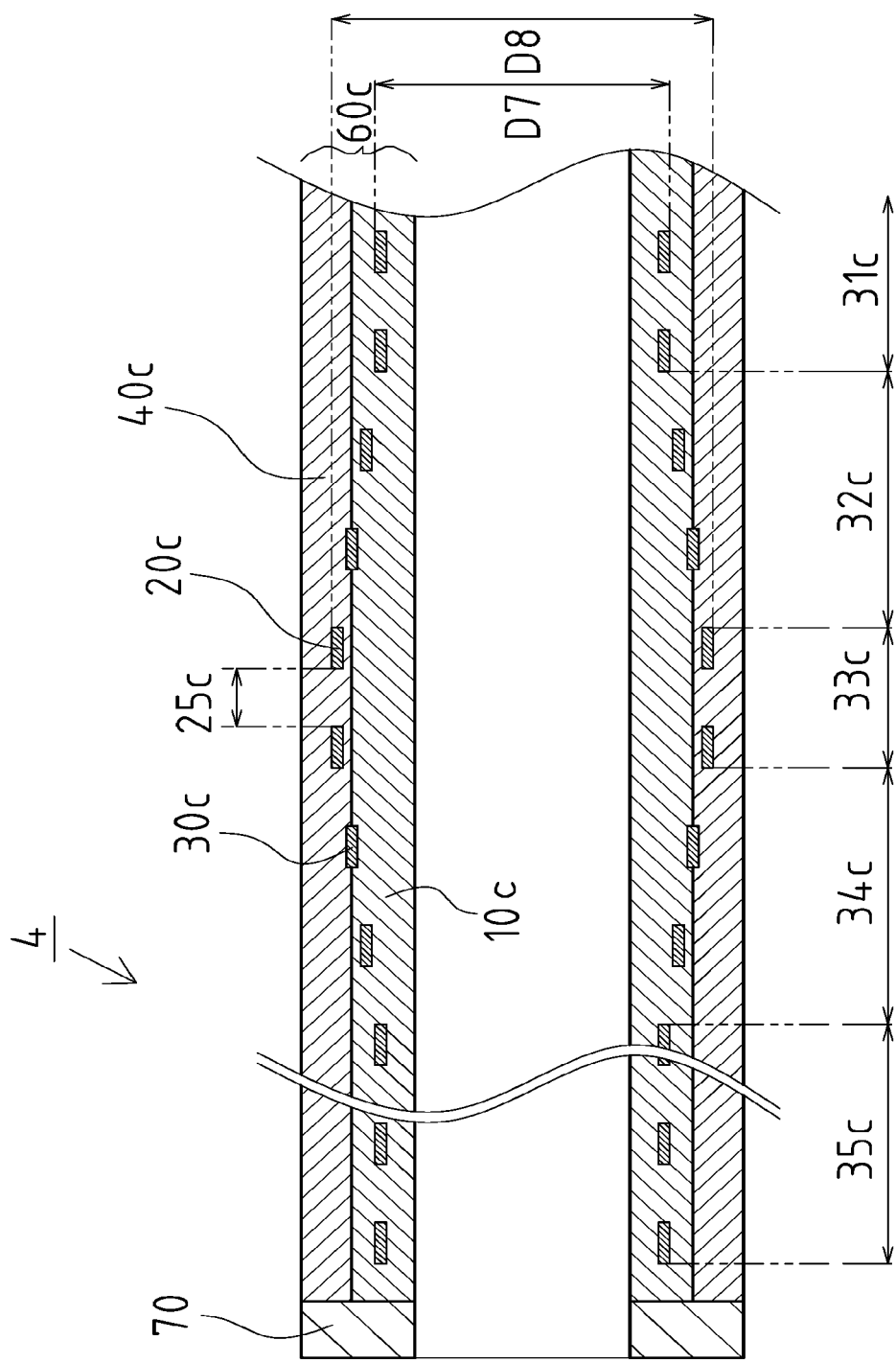
FIG. 7 is a section view corresponding to FIG. 2 of a catheter according to a fourth embodiment.

Next, a catheter 4 of the fourth embodiment will be described with reference to FIG. 7. Explaining only a difference from the catheter 1 illustrated in FIG. 2, in the catheter 4, a catheter shaft 60c includes, in the order from the inner side in a radial direction, a reinforcing body (coil body) 30c wound by a wire 20c so as to have a gap 25c between the adjacent wire 20c, an inner layer 10c covering a part of an outer periphery of the reinforcing body (coil body) 30c, and an outer layer 40c covering an outer periphery of the inner layer 10c. The reinforcing body (coil body) 30c is formed integrally including a small diameter portion 31c and a small diameter portion 35c having a first outer diameter D7, a large diameter portion 33c having a second outer diameter D8 larger than the first outer diameter D7, a tapered portion 32c increasing in diameter toward the distal end side between the small diameter portion 31c and the large diameter portion 33c, and a tapered portion 34c increasing in diameter toward the proximal end side between the small diameter portion 35c and the large diameter portion 33c. The reinforcing body (coil body) 30c is raised from the inside of the inner layer 10c and embedded in the outer layer 40c at the large diameter portion 33c or at the tapered portion 32c, the large diameter portion 33c, and the tapered portion 34c.

In the catheter 4, the reinforcing body (coil body) 30c increases in diameter from the small diameter portion 31c and the small diameter portion 35c toward the large diameter portion 33c. The anchoring effect between the outer layer 40c and the wire 20c embedded therein, at the large diameter portion 33c or at the tapered portion 32c, the large diameter portion 33c, and the tapered portion 34c, can reduce a risk that the outer layer 40c is separated from the inner layer 10c even in the case where the outer layer 40c is pulled in the axis direction (distal end direction and proximal end direction) by a constricted portion or a blocked portion when the catheter 4 is inserted to a blood vessel, a bile duct, a pancreatic duct, or the like.

Note that the catheter 4 may be formed integrally so that the reinforcing body (coil body) 30c does not provide the tapered portion 32c and the small diameter portion 31c, and includes the small diameter portion 35c having the first outer diameter D7, the large diameter portion 33c having the second outer diameter D8 larger than the first outer diameter D7, and the tapered portion 34c increasing in diameter toward the proximal end side between the small diameter portion 35c and the large diameter portion 33c. Then, the reinforcing body (coil body) 30c may be raised from the inside of the inner layer 10c and embedded in the outer layer 40c at the large diameter portion 33c or at the tapered portion 34c and the large diameter portion 33c.

Next, a catheter 5 of the fifth embodiment will be described with reference to FIG. 8. Explaining only a difference from the catheter 4 illustrated in FIG. 7, the catheter 5 includes, in the order from the inner side in a radial direction of a catheter shaft 60d, a reinforcing body (braid) 30d formed by mutually weaving a plurality of wires (a first wire 20d and a second wire 21d) so as to have a gap 25d between the adjacent first wire 20d or between the adjacent second wire 21d, an inner layer 10d covering a part of an outer periphery of the reinforcing body (braid) 30d, and an outer layer 40d covering the inner layer 10d.

Figure 8:
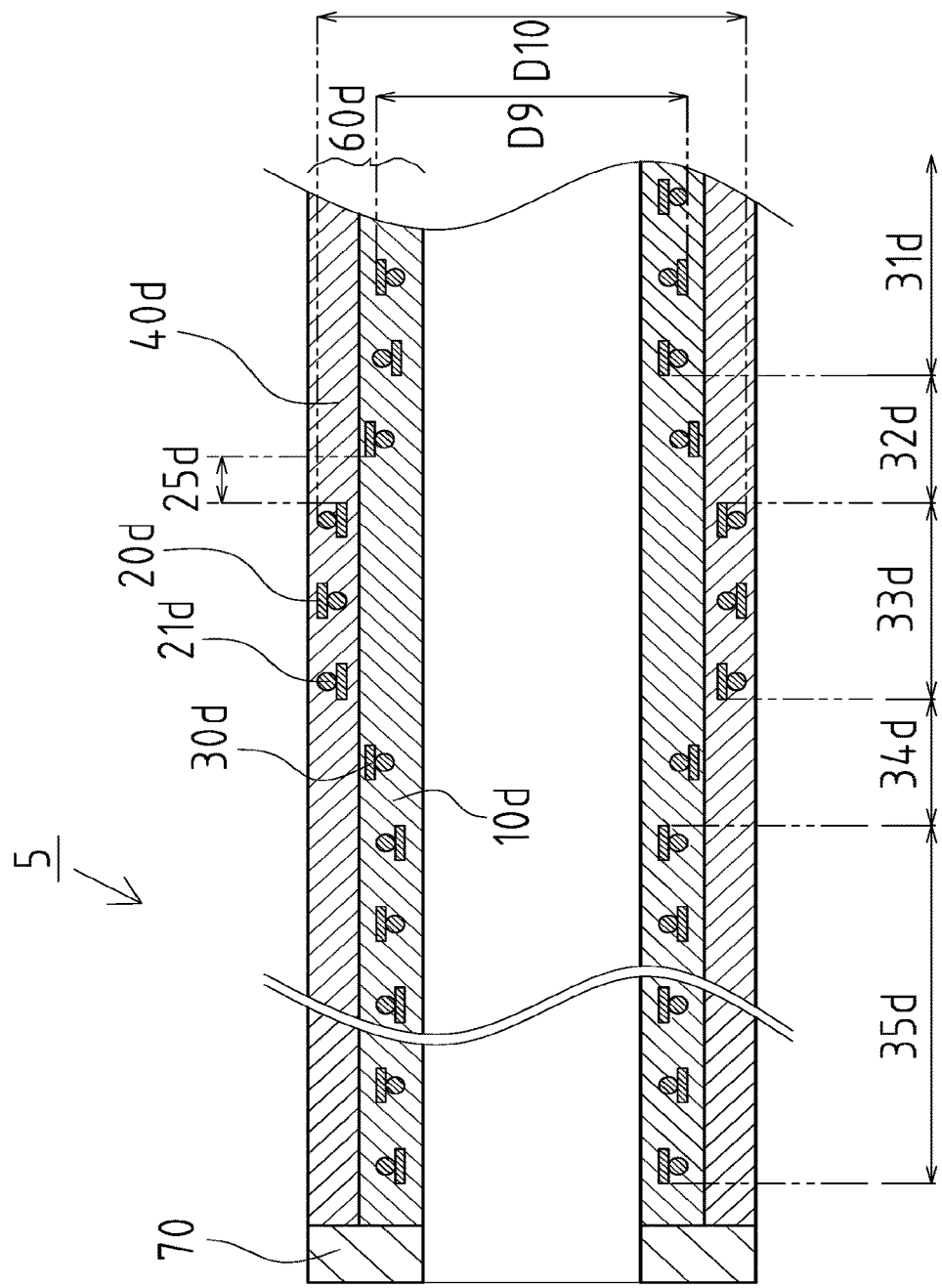
FIG. 8 is a section view corresponding to FIG. 2 of a catheter according to a fifth embodiment.

As illustrated in FIG. 8, in the catheter 5, the reinforcing body (braid) 30d is formed integrally including a small diameter portion 31d and a small diameter portion 35d having a first outer diameter D9, a large diameter portion 33d having D10 larger than the first outer diameter D9, a tapered portion 32d increasing in diameter toward the distal end side between the small diameter portion 31d and the large diameter portion 33d, and a tapered portion 34d increasing in diameter toward the proximal end side between the small diameter portion 35d and the large diameter portion 33d. The reinforcing body (coil body) 30d is raised from the inside of the inner layer 10d and embedded in the outer layer 40d at the large diameter portion 33d or at the tapered portion 32d, the tapered portion 34d, and the large diameter portion 33d.

In the catheter 5, the reinforcing body (braid) 30d increases in diameter from the small diameter portion 31d and the small diameter portion 35d toward the large diameter portion 33d. The anchoring effect between the outer layer 40d and the first wire 20d and the second wire 21d embedded therein, at the large diameter portion 33d or at the tapered portion 32d, the tapered portion 34d, and the large diameter portion 33d, can reduce a risk that the outer layer 40d is separated from the inner layer 10d even in the case where the outer layer 40d is pulled in the axis direction (distal end direction and proximal end direction) by a constricted portion or a blocked portion when the catheter 5 is inserted to a blood vessel, a bile duct, a pancreatic duct, or the like.

Note that the catheter 5 may be formed integrally so that the reinforcing body (braid) 30d does not provide the tapered portion 32d and the small diameter portion 31d, and includes the small diameter portion 35d having the first outer diameter D9, the large diameter portion 33d having the second outer diameter D10 larger than the first outer diameter D9, and the tapered portion 34d increasing in diameter toward the proximal end side between the small diameter portion 35d and the large diameter portion 33d. The reinforcing body (braid) 30d may be raised from the inside of the inner layer 10d and embedded in the outer layer 40d at the large diameter portion 33d or at the tapered portion 34d and the large diameter portion 33d.

Figure 10:
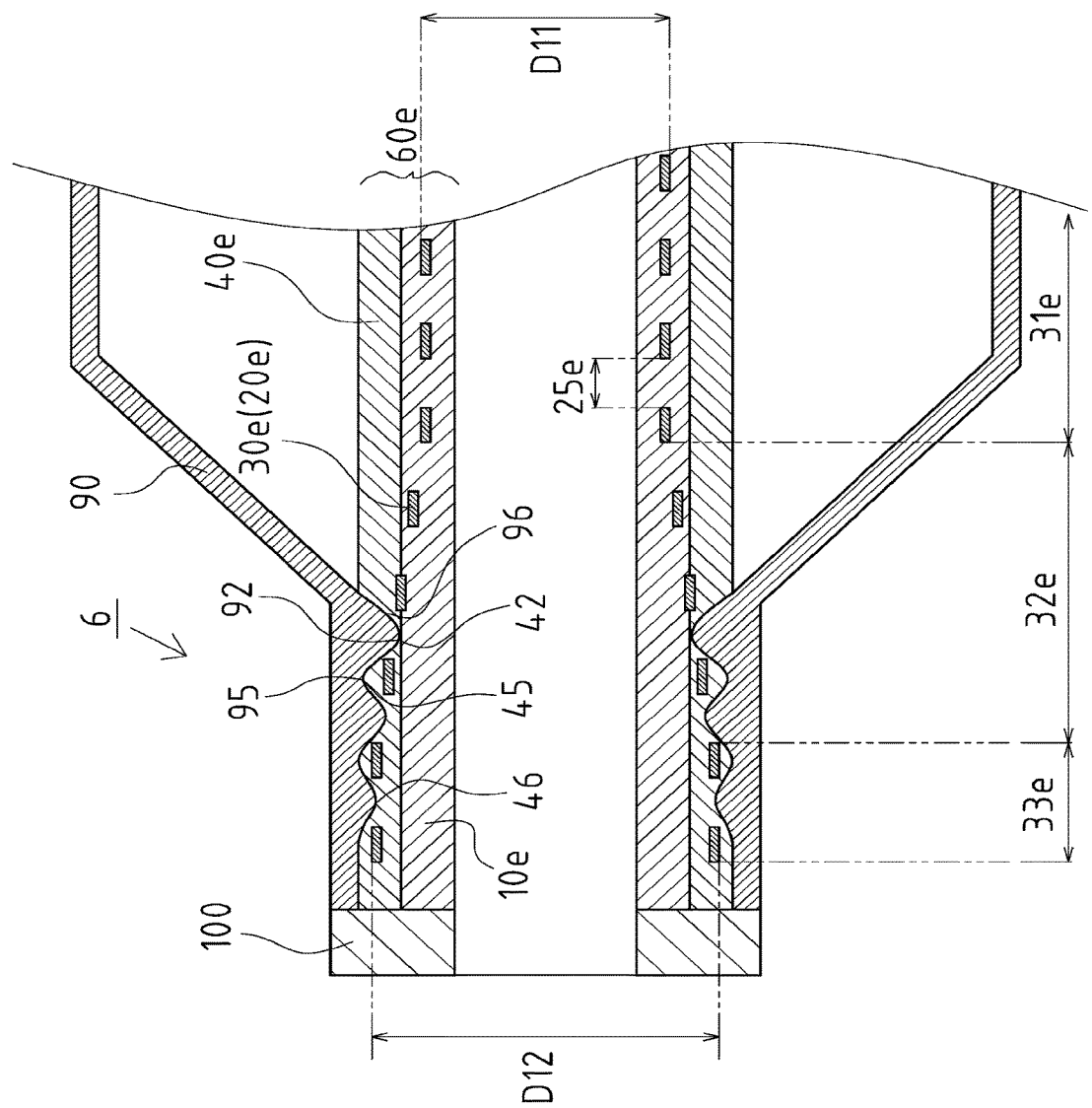
FIG. 10 is an enlarged section view of a B part of FIG. 9.
Figure 11:
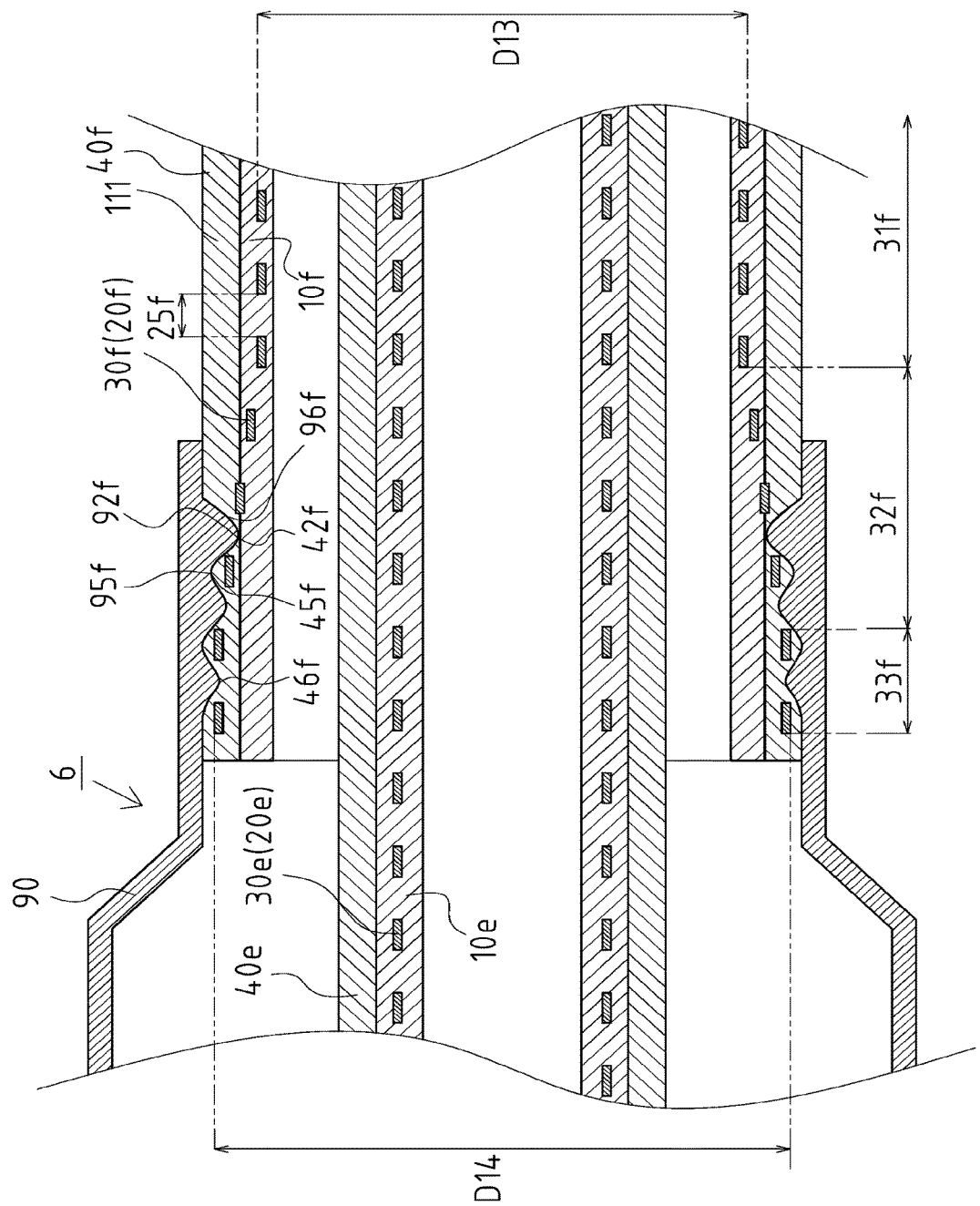
FIG. 11 is an enlarged section view of a C part of FIG. 9.

Next, a balloon catheter 6 of the sixth embodiment will be described with reference to FIG. 9, FIG. 10, and FIG. 11. FIG. 10 is an enlarged view of a B part of FIG. 9. FIG. 11 is an enlarged view of a C part of FIG. 11. The balloon catheter 6 is a medical treatment balloon catheter used for expanding a constricted portion or a blocked portion for treatment, for example.

Figure 9:
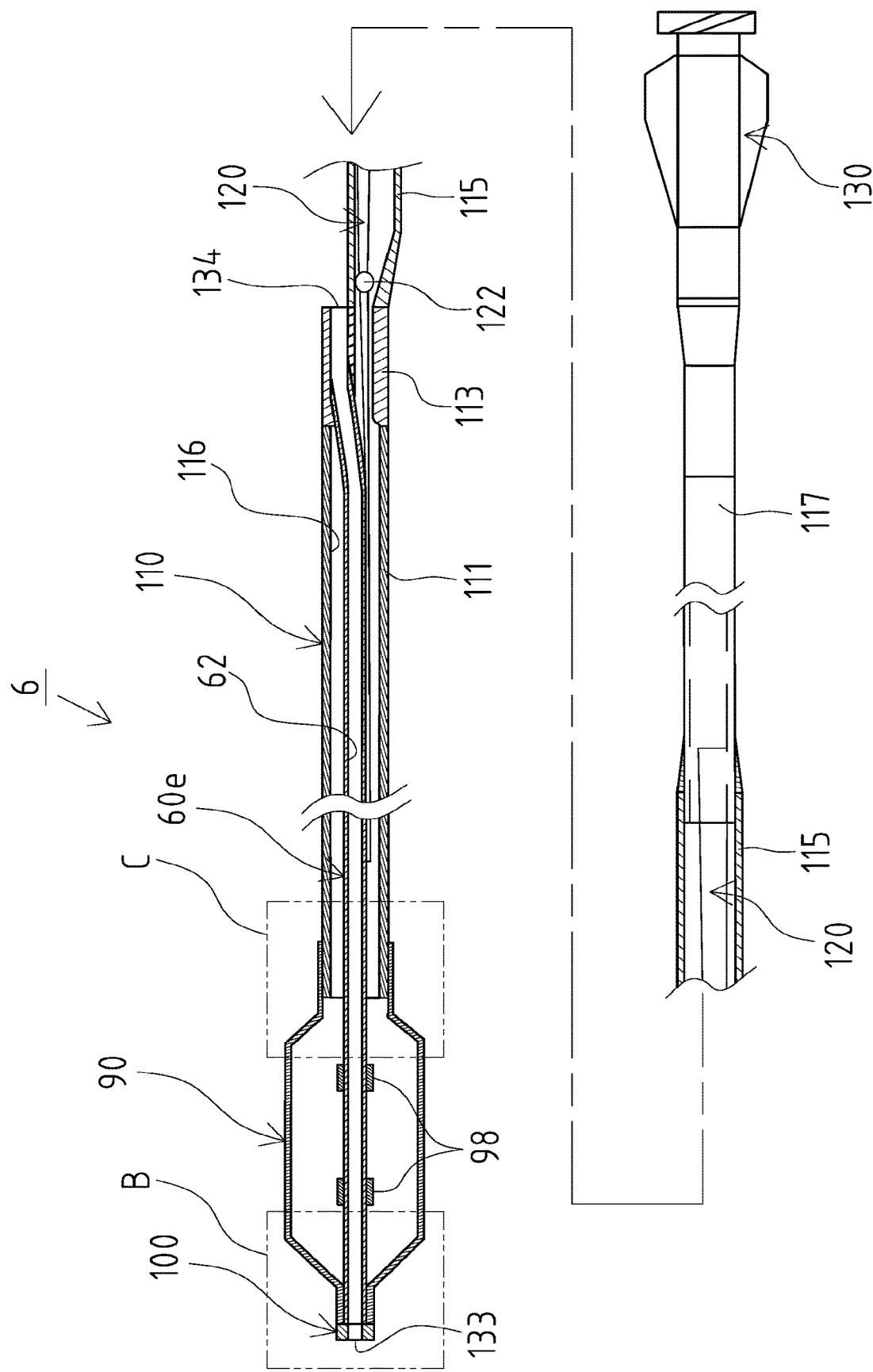
FIG. 9 is a schematic block diagram illustrating the entire of a balloon catheter according to a sixth embodiment.

As illustrated in FIG. 9, the balloon catheter 6 mainly includes a balloon 90, a tip 100, an outer shaft 110, an inner shaft 60e, a core wire 120, and a connector 130.

The balloon 90 expanding a constricted portion or a blocked portion is formed of a resin member. A distal end of the balloon 90 is joined to a distal end of the inner shaft 60e and a proximal end of the tip 100. A proximal end of the balloon 90 is joined to a distal end of the outer shaft 110.

The outer shaft 110 is a tubular member configuring an expanded lumen 116 for supplying liquid such as a contrast medium or physiological saline to expand the balloon 90. The outer shaft 110 includes, in the order from the distal end side, a distal end outer shaft part 111, a guide wire port part 113, an intermediate outer shaft part 115, and a proximal end outer shaft part 117. The distal end outer shaft part 111 and the intermediate outer shaft part 115 are tubes formed of resin such as polyamide, polyamide elastomer, polyolefin, polyester, and polyester elastomer. The guide wire port part 113 is a part where the distal end outer shaft part 111, the intermediate outer shaft part 115, and the inner shaft 60e are joined to one another.

The inner shaft 60e is inserted to the distal end outer shaft part 111, and the above-described lumen 116 is formed between the distal end outer shaft part 111 and the inner shaft 60e.

The proximal end outer shaft part 117 is a metallic tubular member of a so-called hypo tube. The distal end of the proximal end outer shaft part 117 is inserted and joined to the proximal end of the intermediate outer shaft part 115. The connector 130 is attached to the proximal end of the proximal end outer shaft part 117. When liquid such as a contrast medium or physiological saline for expanding the balloon 90 is supplied from an indeflator (not illustrated) that can be attached to the connector 130, the liquid passes through the expanded lumen 116 to expand the balloon 90. Note that a material of the proximal end outer shaft part 117 is not particularly limited, and stainless steel (SUS302, SUS304) or a superelastic alloy such as an Ni—Ti alloy can be used.

The inner shaft 60e includes a guide wire lumen 62 through which a guide wire is inserted. The proximal end of the inner shaft 60e is joined to the guide wire port part 113 of the outer shaft 110 to form a proximal end side guide wire part 134. A technician can replace a guide wire through the proximal end side guide wire port 134.

The tip 100 is joined to the frond end of the inner shaft 60e and the distal end of the balloon 90. The tip 100 is formed of flexible resin. The material is not particularly limited, and polyurethane, polyurethane elastomer, or the like can be used. Moreover, the tip 100 includes a distal end side guide wire port 133 at the distal end thereof.

The core wire 120 is attached on the inner periphery of the distal end of the proximal end outer shaft part 117. The core wire 120 has a circular section, and is tapered metal wire reducing in diameter toward the distal end. The material of the core wire 120 is not particularly limited, and stainless steel (SUS304) or a superelastic alloy such as an Ni—Ti alloy can be used. The core wire 120 passes the intermediate outer shaft part 115 and the guide wire port part 113 and extends to the distal end outer shaft part 111. Moreover, the core wire 120 provides a pusher part 122 that can be in contact with the guide wire port part 113.

In the balloon 90, two markers 98 are attached on an outer periphery of the inner shaft 60e. In this manner, a technician such as a physician can accurately grasp a position of the balloon 90 in X-ray irradiation and, as a result, it becomes easy to securely expand a constricted portion or a blocked portion.

As illustrated in FIG. 10, the inner shaft 60e includes, in the order from the inner side in a radial direction, a reinforcing body (coil body) 30e wound by a wire 20e so as to have a gap 25e between the adjacent wire 20e, an inner layer 10e covering an outer periphery of the reinforcing body (coil body) 30e, and an outer layer 40e covering an outer periphery of the inner layer 10e. Note that the inner shaft 60e corresponds to the catheters 1 to 5 of the above-described first to fifth embodiments.

The reinforcing body 30e is formed integrally including a small diameter portion 31e having a first outer diameter D11, a large diameter portion 33e having a second outer diameter D12 larger than the first outer diameter D11, which is provided on the distal end side than the small diameter portion 31e, and a tapered portion 32e increasing in diameter toward the distal end side between the small diameter portion 31e and the large diameter portion 33e. The reinforcing body (coil body) 30e is raised from the inside of the inner layer 10e and embedded in the outer layer 40e at the large diameter portion 33e or at the tapered portion 32e and the large diameter portion 33e.

In the inner shaft 60e, the reinforcing body 30e increases in diameter from the small diameter portion 31e toward the large diameter portion 33e. The anchoring effect between the outer layer 40e and the wire 20e embedded therein, at the large diameter portion 33e or at the tapered portion 32e and the large diameter portion 33e, can reduce a risk that the outer layer 40e is separated from the inner layer 10e even in the case where the balloon 90 and the outer layer 40e are pulled in the axis direction (distal end direction and proximal end direction) when the balloon catheter 6 is inserted to a blood vessel, a bile duct, a pancreatic duct, or the like.

Furthermore, at the joint portion between the outer layer 40e and the balloon 90, the outer layer 40e has a concave and convex outer peripheral surface 46 including concave portions 42 and convex portions 45, and the balloon 90 includes a concave and convex inner peripheral surface 96 including concave portions 95 and convex portions 92 corresponding to the outer peripheral surface 46 of the outer layer 40e. At the large diameter portion 33e of the reinforcing body (coil body) 30e or at the tapered portion 32e and the large diameter portion 33e, the convex portions 92 of the balloon 90 are embedded to the inner layer 10e side than the second outer diameter D12 of the reinforcing body 30e in the gap 25e between the wire 20e. In other words, the inner diameter at the convex portion 92 of the balloon 90 is smaller than the second outer diameter D12 of the large diameter portion 33e of the reinforcing body (coil body) 30e.

In this manner, the convex portion 92 of the balloon 90 is joined to the concave portion 42 of the outer layer 40e, and the concave portion 95 of the balloon 90 is joined to the convex portion 45 of the outer layer 40e, which increases a joint area between the balloon 90 and the outer layer 40e and improves the joint strength. Therefore, even in the case where the balloon 90 is expanded in the radial direction, it is possible to reduce a risk that the balloon 90 is separated from the outer layer 40e.

Furthermore, at the large diameter portion 33e of the reinforcing body (coil body) 30e or at the tapered portion 32e and the large diameter portion 33e, the convex portion 92 of the balloon 90 is embedded to the inner layer 10e side than the second outer diameter D12 in the gap 25e between the wire 20e (in other words, the inner diameter at the convex portion 92 of the balloon 90 is smaller than the second outer diameter D12.) In this manner, even in the case where the balloon 90 is expanded in the radial direction and the axis direction, the convex portion 92 of the balloon 90 is caught by the wire 20e embedded in the outer layer 40e, which reduces a risk that the balloon 90 is separated from the outer layer 40e. Note that the embedding depth of the convex portions 92 of the balloon 90 in the gaps 25e may be equal or different partially.

As illustrated in FIG. 11, the proximal end of the balloon 90 is joined to the distal end of the distal end outer shaft part 111.

The distal end outer shaft part 111 includes, in the order from the inner side in a radial direction, a reinforcing body (coil body) 30f wound by a wire 20f to have a gap 25f between the adjacent wire 20f, an inner layer 10f covering an outer periphery of the reinforcing body (coil body) 30f, and an outer layer 40f covering an outer periphery of the inner layer 10f. Note that the outer shaft part 111 corresponds to the catheters 1 to 5 of the above-described first to fifth embodiments.

The reinforcing body (coil body) 30f is formed integrally including a small diameter portion 31f having a first outer diameter D13, a large diameter portion 33f having a second outer diameter D14 larger than the first outer diameter D13, which is provided on the distal end side than the small diameter portion 31f, and a tapered portion 32f increasing in diameter toward the distal end side between the small diameter portion 31f and the large diameter portion 33f. The reinforcing body (coil body) 30f is raised from the inside of the inner layer 10f and embedded in the outer layer 40f at the large diameter portion 33f or at the tapered portion 32f and the large diameter portion 33f.

In the distal end outer shaft part 111, the reinforcing body (coil body) 30f increases in diameter from the small diameter portion 31f toward the large diameter portion 33f. The anchoring effect between the outer layer 40f and the reinforcing body (coil body) 30f embedded therein, at the large diameter portion 33f or at the tapered portion 32f and the large diameter portion 33f, can reduce a risk that the balloon 90 is separated from the distal end outer shaft part 111 even in the case where the balloon 90 and the outer layer 40f are pulled in the axis direction (distal end direction and proximal end direction) when the balloon catheter 6 is inserted to a blood vessel, a bile duct, a pancreatic duct, or the like, or in the case where the balloon 90 is expanded in the radial direction.

Furthermore, at the joint portion between the outer layer 40f and the balloon 90, the outer layer 40f has a concave and convex outer peripheral surface 46f including concave portions 42f and convex portions 45f, and the balloon 90 has a concave and convex inner peripheral surface 96f including concave portions 95f and convex portions 92f corresponding to the outer peripheral surface 46f of the outer layer 40f. At the large diameter portion 33f of the reinforcing body (coil body) 30f or at the tapered portion 32f and the large diameter portion 33f, the convex portion 92f of the balloon 90 is embedded to the inner layer 10f side than the second outer diameter D14 of the reinforcing body 30f in the gap 25f between the wire 20f. In other words, the inner diameter at the convex portion 92f of the balloon 90 is smaller than the second outer diameter D14 of the large diameter portion 33f of the reinforcing body (coil body) 30f.

In this manner, the convex portion 92f of the balloon 90 is joined to the concave portion 42f of the outer layer 40f, and the concave portion 95f of the balloon 90 is joined to the convex portion 45f of the outer layer 40f, which increases a joint area between the balloon 90 and the outer layer 40f and improves the joint strength. Therefore, even in the case where the balloon 90 is expanded in the radial direction and the axis direction, it is possible to reduce a risk that the balloon 90 is separated from the distal end outer shaft part 111.

Furthermore, at the large diameter portion 33f of the reinforcing body (coil body) 30f, or at the tapered portion 32f and the large diameter portion 33f, the convex portion 92f of the balloon is embedded to the inner layer 10f side than the second outer diameter D14 in the gap 25f of the wire 20f (in other words, the inner diameter at the convex portion 92f of the balloon 90 is smaller than the second outer diameter D14). Thus, even in the case where the balloon 90 is expanded in the radial direction and the axis direction, the convex portion 92f of the balloon 90 is caught by the wire 20f embedded in the outer layer 40f, which can reduce a risk that the balloon 90 is separated from the outer layer 40f. Note that the embedding depth of the convex portions 92f of the balloon 90 in the gaps 25f may be equal or different partially.

Note that the balloon catheter 6 includes the joint portion between the inner shaft 60e and the balloon 90 illustrated in FIG. 10 and the joint portion between the distal end outer shaft part 111 and the balloon 90 illustrated in FIG. 11. However, the embodiment is not limited thereto. The balloon catheter 6 may include one of the joint portion between the inner shaft 60e and the balloon 90 illustrated in FIG. 10 and the joint portion between the distal end outer shaft part 111 and the balloon 90 illustrated in FIG. 11.

Figure 12:
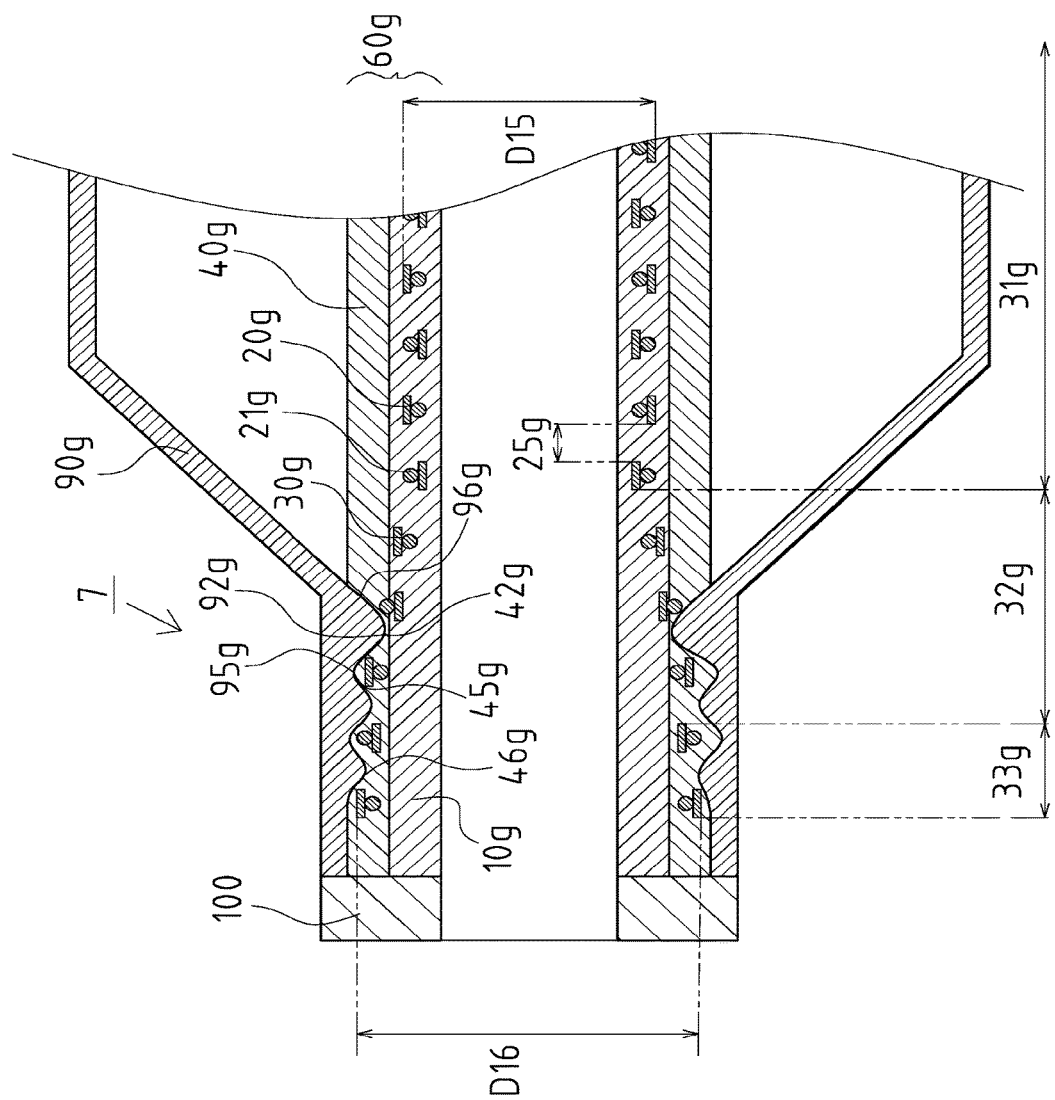
FIG. 12 is a section view corresponding to FIG. 10 of a balloon catheter according to a seventh embodiment.

Next, a balloon catheter 7 of the seventh embodiment will be described with reference to FIG. 12. Explaining only a difference from the balloon catheter 6 illustrated in FIG. 10, the balloon catheter 7 includes, in the order from the inner side in a radial direction of an inner shaft 60g, a reinforcing body (braid) 30g formed by mutually weaving a plurality of wires (a first wire 20g and a second wire 21g) to have a gap 25g between the adjacent first wire 20g or between the adjacent second wire 21g, an inner layer 10g covering an outer periphery of the reinforcing body (braid) 30g, and an outer layer 40g covering the inner layer 10g. Note that the inner shaft 60g corresponds to the catheters 1 to 5 of the above-described first to fifth embodiments.

The reinforcing body (braid) 30g is formed integrally including a small diameter portion 31g having a first outer diameter D15, a large diameter portion 33g having a second outer diameter D16 larger than the first outer diameter D15, which is provided on the distal end side than the small diameter portion 31g, and a tapered portion 32g increasing in diameter toward the distal end side between the small diameter portion 31g and the large diameter portion 33g. The reinforcing body (braid) 30g is raised from the inside of the inner layer 10g and embedded in the outer layer 40g at the large diameter portion 33g or at the tapered portion 32g and the large diameter portion 33g.

In the inner shaft 60g, the reinforcing body (braid) 30g increases in diameter from the small diameter portion 31g toward the large diameter portion 33g. The anchoring effect between the outer layer 40g and the reinforcing body (braid) 30g embedded therein, at the large diameter portion 33g or at the tapered portion 32g and the large diameter portion 33g, can reduce a risk that the outer layer 40g is separated from the inner layer 10g even in the case where the balloon 90g and the outer layer 40g are pulled in the axis direction (distal end direction and proximal end direction) when the balloon catheter 7 is inserted to a blood vessel, a bile duct, a pancreatic duct, or the like.

Furthermore, at the joint portion between the outer layer 40g and the balloon 90g, the outer layer 40g has a concave and convex outer peripheral surface 46g including concave portions 42g and convex portions 45g, and the balloon 90g has a concave and convex inner peripheral surface 96g including concave portions 95g and convex portions 92g corresponding to the outer peripheral surface 46g of the outer layer 40g. At the large diameter portion 33g of the reinforcing body (braid) 30g or at the tapered portion 32g and the large diameter portion 33g, the convex portion 92g of the balloon 90g is embedded to the inner layer 10g side than the second outer diameter D16 of the reinforcing body 30g in the gap 25g of the reinforcing body (braid) 30g. In other words, the inner diameter at the convex portion 92g of the balloon 90g is smaller than the second outer diameter D16 of the large diameter portion 33g of the reinforcing body (braid) 30g.

In this manner, the convex portion 92g of the balloon 90g is joined to the concave portion 42g of the outer layer 40g, and the concave portion 95g of the balloon 90g is joined to the convex portion 45g of the outer layer 40g, which increases a joint area between the balloon 90g and the outer layer 40g and improves the joint strength. Therefore, even in the case where the balloon 90g is expanded in the radial direction and the axis direction, it is possible to reduce a risk that the balloon 90g is separated from the outer layer 40g.

Furthermore, at the large diameter portion 33g of the reinforcing body (braid) 30g, or at the tapered portion 32g and the large diameter portion 33g, the convex portion 92g of the balloon 90g is embedded to the inner layer 10g side than the second outer diameter D16 in the gap 25g of the wire 20g (in other words, the inner diameter at the convex portion 92g of the balloon 90g is smaller than the second outer diameter D16). Thus, even in the case where the balloon 90g is expanded in the radial direction and the axis direction, the convex portion 92g of the balloon 90g is caught by the wire 20g embedded in the outer layer 40g, which can reduce a risk that the balloon 90g is separated from the outer layer 40g. Note that the embedding depth of the convex portions 92g of the balloon 90g in the gaps 25g may be equal or different partially.

Figure 13:
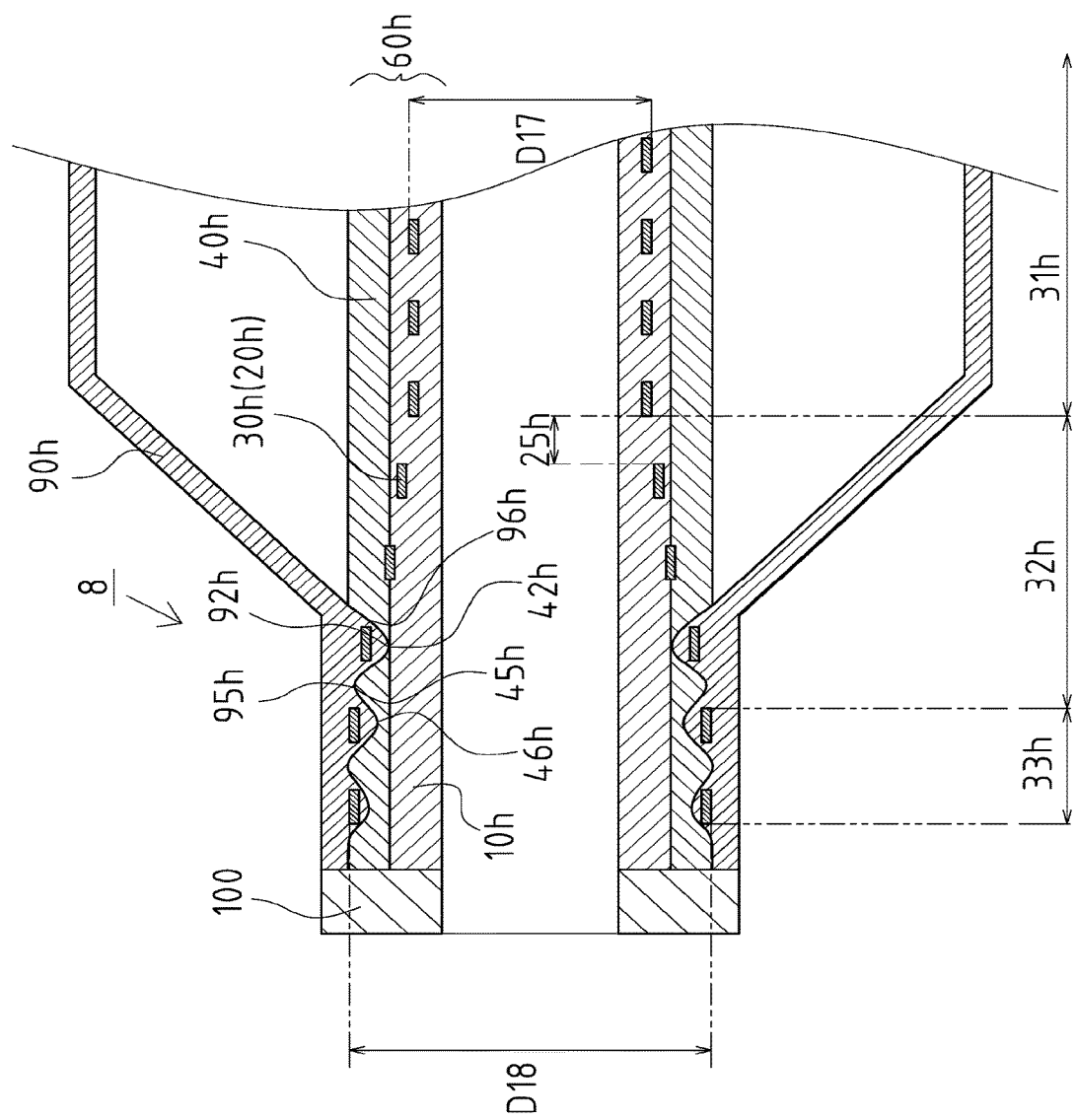
FIG. 13 is a section view corresponding to FIG. 10 of a balloon catheter according to an eighth embodiment.

Next, a balloon catheter 8 of the eighth embodiment will be described with reference to FIG. 13. Explaining only a difference from the balloon catheter 6 illustrated in FIG. 10, the balloon catheter 8 provides, in the order from the inner side in a radial direction, a reinforcing body (coil body) 30h wound by a wire 20h so as to have a gap 25h between the adjacent wire 20h, an inner layer 10h covering an outer periphery of the reinforcing body (coil body) 30h, an outer layer 40h covering an outer periphery of the inner layer 10h, and a balloon 90h joined to an outer periphery of the outer layer 40h, as illustrated in FIG. 13.

Note that although a resin layer 60h includes two layers of the inner layer 10h and the outer layer 40h in the balloon catheter 8, the embodiment is not limited thereto. The resin layer may include only one layer of the outer layer 40h.

The reinforcing body (coil body) 30h is formed integrally including a small diameter portion 31h having a first outer diameter D17, a large diameter portion 33h having a second outer diameter D18 larger than the first outer diameter D17, which is provided on the distal end side than the small diameter portion 31h, and a tapered portion 32h increasing in diameter toward the distal end side between the small diameter portion 31h and the large diameter portion 33h.

Furthermore, at the joint portion between the outer layer 40h and the balloon 90h, the outer layer 40h has a concave and convex outer peripheral surface 46h including concave portions 42h and convex portions 45h, and the balloon 90h includes a concave and convex inner peripheral surface 96h including concave portions 95h and convex portions 92h corresponding to the outer peripheral surface 46h of the outer layer 40h.

At the large diameter portion 33h or at the tapered portion 32h and the large diameter portion 33h, the reinforcing body (coil body) 30h is raised from the inside of the inner layer 10h and the outer layer 40h and embedded in the convex portions 92h of the balloon 90h.

In the resin layer 60h, the reinforcing body (coil body) 30h increases in diameter from the small diameter portion 31h toward the large diameter portion 33h. The anchoring effect with the reinforcing body 30h embedded in the convex portion 92h of the balloon 90h, at the large diameter portion 33h or at the tapered portion 32h and the large diameter portion 33h, can reduce a risk that the balloon 90h is separated from the outer layer 40h even in the case where the balloon 90h is pulled in the axis direction (distal end direction and proximal end direction) when the balloon catheter 8 is inserted to a blood vessel, a bile duct, a pancreatic duct, or the like, or in the case where the balloon 90h is expanded in the radial direction.

Furthermore, the convex portion 92h of the balloon 90h is joined to the concave portion 42h of the outer layer 40h and the concave portion 95h of the balloon 90h is joined to the convex portion 45h of the outer layer 40h, which increases a joint area between the balloon 90h and the outer layer 40h and improves the joint strength. Therefore, even in the case where the balloon 90h is expanded in the radial direction and the axis direction, it is possible to reduce a risk that the balloon 90h is separated from the outer layer 40h.

Note that the balloon 90 and the distal end outer shaft part 111 of the balloon catheter 6 illustrated in FIG. 11 may be applied to the balloon catheters 7 and 8 of the seventh and eighth embodiments.

Moreover, in the catheters 1 to 3, the reinforcing bodies 30 to 30b include the tapered portions 32 to 32b increasing in diameter toward the distal end side. However, they may include the tapered portions increasing in diameter toward the proximal end side.

In addition, in the above description, the coil body and the braid are exemplified as the reinforcing bodies 30 to 30h. However, the embodiment is not limited thereto. For example, as the reinforcing bodies 30 to 30h of the catheters 1 to 5 and the balloon catheters 6 to 8, a hypo tube (metal tube) may be provided with helical slits to form a reinforcing layer with these slits as gaps.

DESCRIPTION OF SYMBOLS

1 to 5 catheter
6 to 8 balloon catheter
10 to 10h inner layer
20 to 20h, 21b, 21d wire
25 to 25h gap between wire
30 to 30h reinforcing body
31 to 31h, 35c, 35d small diameter portion
32 to 32h, 34c, 34d tapered portion
33 to 33h large diameter portion
40 to 40h outer layer
42, 42f to 42h outer peripheral surface concave portion of outer layer
45, 45f to 45h outer peripheral surface convex portion of outer layer
46, 46f to 46h outer peripheral surface of outer layer
60 to 60d catheter shaft
60e, 60g inner shaft
60h resin layer
70, 100 tip
80, 130 connector
90, 90g, 90h balloon
92, 92f to 92h inner peripheral surface convex portion of balloon
95, 95f to 95h inner peripheral surface concave portion of balloon
96, 96f to 96h inner peripheral surface of balloon
110 outer shaft
111 distal end outer shaft part

The invention claimed is:

1. A catheter, comprising:
   a reinforcing body including a wire wound or woven such that a gap is formed between each winding or weave of the wire;
   an inner layer extending in a longitudinal direction such that the reinforcing body has a first diameter portion embedded in the inner layer; and
   an outer layer covering an outer periphery of the inner layer in a circumferential direction,
   wherein the reinforcing body has the first diameter portion with a first outer diameter, a second diameter portion with a second outer diameter larger than the first outer diameter of the first diameter portion, and a tapered portion increasing in diameter toward a distal end side from the first diameter portion to the second diameter portion, the tapered portion of the reinforcing body has a distal end side portion embedded in the outer layer, and a proximal end side portion embedded in the inner layer such that the tapered portion is extending from the inner layer to the outer layer, and the second diameter portion of the reinforcing body is embedded in the outer layer such that the outer layer is surrounding the second diameter portion of the reinforcing body in the circumferential direction.

2. The catheter according to claim 1, wherein at least one of the first diameter portion and the second diameter portion extends in the longitudinal direction.

3. The catheter according to claim 1, wherein at least one of the inner layer and the outer layer comprises resin.

4. The catheter according to claim 1, wherein the reinforcing body comprises at least one of metal and resin.

5. The catheter according to claim 1, wherein the reinforcing body comprises a coil body comprising at least one of metal and resin.

6. The catheter according to claim 1, wherein the outer layer comprises resin, and the inner layer comprises resin.

7. The catheter according to claim 1, wherein the outer layer comprises resin selected from the group consisting of polyamide, polyamide elastomer, polyester, polyurethane and polyethylene, and the inner layer comprises resin selected from the group consisting of polyamide, polyamide elastomer, polyester, polyurethane, and polyethylene.

8. The catheter according to claim 1, wherein the reinforcing body includes a plurality of wires.

9. The catheter according to claim 8, wherein the plurality of wires includes at least two wires in a mesh form in which the at least two wires are wound or woven in an opposite direction with each other.

10. The catheter according to claim 1, wherein the reinforcing body includes a plurality of wires including at least one of a flat wire and a round wire.

11. The catheter according to claim 1, further comprising: a tip positioned at the distal end side of the catheter in the longitudinal direction.

12. A balloon catheter, comprising:
a catheter comprising a reinforcing body including a wire wound or woven such that a gap is formed between each winding or weave of the wire, an inner layer extending in a longitudinal direction such that the reinforcing body has a first diameter portion embedded in the inner layer and having a first outer diameter, and an outer layer covering an outer periphery of the inner layer in a circumferential direction such that the reinforcing body has a second diameter portion embedded in the outer layer and having a second outer diameter;
a balloon joined to the outer layer of the catheter such that the balloon is positioned on a side of the second diameter portion of the reinforcing body of the catheter and has an inner peripheral surface having a concave portion and a convex portion and that an inner diameter of the convex portion is smaller than the second outer diameter of the second diameter portion of the reinforcing body at at least one gap between adjacent windings of the wire in the second diameter portion in the longitudinal direction,
wherein the reinforcing body has the second diameter portion with the second outer diameter larger than the first outer diameter of the first diameter portion, and a tapered portion increasing in diameter toward a distal end side from the first diameter portion to the second diameter portion, the tapered portion of the reinforcing body has a distal end side portion embedded in the outer layer, and a proximal end side portion embedded in the inner layer such that the tapered portion is extending from the inner layer to the outer layer, and the second diameter portion of the reinforcing body is embedded in the outer layer such that the outer layer is surrounding the second diameter portion of the reinforcing body in the circumferential direction.

13. The balloon catheter according to claim 12, wherein the inner diameter of the convex portion is an inner diameter of a tip of the convex portion.

14. The balloon catheter according to claim 12, wherein at least a tip of the convex portion is embedded further inward than the second diameter portion in the circumferential direction.

15. The balloon catheter according to claim 12, further comprising:
a tip formed at a distal end of the balloon catheter in the longitudinal direction; and
an outer shaft formed such that one end of the balloon in the longitudinal direction is connected to the tip and that an opposite end of the balloon in the longitudinal direction is connected to the outer shaft.

16. The balloon catheter according to claim 15, wherein the convex portion is formed in the one end of the balloon, the balloon has the inner peripheral surface formed such that the inner peripheral surface has a plurality of convex portions including the convex portion in the one end of the balloon such that the inner diameter of the convex portion in the one end of the balloon is smaller than the second outer diameter, and the plurality of convex portions includes a convex portion formed in the opposite end of the balloon in the longitudinal direction such that an inner diameter of the convex portion in the opposite end of the balloon is smaller than the second outer diameter.

17. The balloon catheter according to claim 12, further comprising:
at least two markers formed on an outer periphery of the catheter in an area of the catheter covered by the balloon.

18. The catheter according to claim 12, wherein the reinforcing body includes a plurality of wires including at least one of a flat wire and a round wire.

* * * * *